United States Patent

Loos et al.

[11] Patent Number: 6,094,969
[45] Date of Patent: Aug. 1, 2000

[54] DEVICE FOR CHECKING A CLOSURE OR A CONNECTING WELD FOR TIGHTNESS

[75] Inventors: Johannes Antonius Loos, Aalsmeer; Alex Schippers, Exloo; Jan Bons, Aalsmeer, all of Netherlands

[73] Assignee: NPBI International B.V., Netherlands

[21] Appl. No.: 08/860,734

[22] PCT Filed: Jan. 5, 1996

[86] PCT No.: PCT/NL96/00009

§ 371 Date: Jun. 1, 1998

§ 102(e) Date: Jun. 1, 1998

[87] PCT Pub. No.: WO96/21141

PCT Pub. Date: Jul. 11, 1996

[30] Foreign Application Priority Data

Jan. 6, 1995 [NL] Netherlands .......................... 9500033

[51] Int. Cl.[7] .............................. G01M 3/02; G01B 13/08
[52] U.S. Cl. .................................. 73/37; 73/37.5; 73/49.1
[58] Field of Search ............................ 73/37, 37.5, 49.1; 623/66; 530/356; 606/194; 156/64, 158

[56] References Cited

U.S. PATENT DOCUMENTS 5,674,333 10/1997 Loos et al. ................................ 156/64

FOREIGN PATENT DOCUMENTS

B-78201/87 4/1989 Australia .
898421 4/1945 France .

*Primary Examiner*—Hezron Williams
*Assistant Examiner*—Jay L. Politzer
*Attorney, Agent, or Firm*—Dehlinger & Associates

[57] ABSTRACT

The invention relates to a device for checking for tightness a closure or a connecting weld provided in a flexible fluid-filled hose, which device comprises two clamping members slidable relative to each other, forming in an inserted position a profile with at least one clamping space and an expansion space, as well as folding means, the arrangement being such that at least one hose portion can be folded and clamped in the at least one clamping space, so that the fluid present in the at least one hose portion is pressed to another hose portion including the closure or connecting weld to be checked, which other hose portion can expand in the expansion space.

15 Claims, 4 Drawing Sheets

DEVICE FOR CHECKING A CLOSURE OR A CONNECTING WELD FOR TIGHTNESS

CROSS-REFERENCE TO RELATED APPLICATIONS

This application is a continuation of International Application No. PCT/NL96/00009, filed Jan. 5, 1996, designating the United States, which claims priority to Netherlands Application No. 9500033, filed Jan. 6, 1995. These applications are incorporated herein by reference in their entirety.

FIELD OF THE INVENTION

The invention related to a device for checking the tightness of a closure or a connecting weld provided in a flexible fluid-filled hose.

BACKGROUND OF THE INVENTION

This invention relates to a device for checking the tightness of a closure or a connecting weld provided in a flexible fluid-filled hose, wherein the device comprises two clamping members slidable relative to each other, forming in an inserted position a profile with at least one clamping space and an expansion space, as well as folding elements.

Such a device is known from FR-A-898421. This known device is used for testing the tightness of an air-filled tube from bicycles, motorcycles or others. In use two of these devices are clamped around the tube. Subsequently, the devices are moved towards each other for testing the part of the tube which lays between the devices. Hence, a problem is that at least two devices are required for testing a single tube wherein these devices have to be operated independently from each other.

SUMMARY OF THE INVENTION

The object of the invention is to provide a device for checking for tightness of a closure or a connecting weld provided in a flexible fluid-filled hose which device does not include the above referred to problem.

According to the invention the device further comprises a first and a second clamping space, with the expansion space provided between them, the arrangement being such that a first and a second hose portion can be folded and clamped in the first and second clamping space, so that the fluid present in the first and second hose portion is pressed to a third hose portion which includes the closure or connecting weld to be checked, which third hose portion can expand in the expansion space.

Such a device is intended for use in the treatment and processing of fluids stored in bags or containers, in particular blood. In this connection, it is conventional to transfer the fluid from a first bag or container to a second bag or container, utilizing flexible hoses connected to each bag or container, which hoses, for the purpose of transferring fluid, must be coupled by means of a connecting weld, to be subsequently uncoupled and closed by means of a closure. In this regard, it is of major importance, inter alia in view of the storage life and the sterility of the fluid, that the connecting welds or closures exhibit no holes or faults that may give rise to leakage.

By virtue of the features of the invention, a device is provided which on the one hand is simple and inexpensive to produce and on the other is easy to use during the treatment or processing of a fluid stored in bags or containers.

In order to obtain a uniform clamping of the hose portion, the device is preferably provided with means for the directed displacement of the two clamping members away from and towards each other, for instance pins engaging in guiding openings. In this connection, one of the two clamping members may possess folding elements arranged on the side thereof, which embrace the other clamping member in the condition of mutual abutment and fold the two ends of the hose portion, such that the fluid present in this hose portion is closed off from the remainder of the hose. In the case where leakage occurs in the hose portion to be checked, this hose portion can easily be closed off on both sides and subsequently be removed, in such a manner that the fluid present in the containers is saved.

In order to facilitate placement of the hose portion to be checked, the first and the second clamping space preferably have the same width, with at least one of the two clamping members being provided at its top surface with an auxiliary line for centric placement of the connecting weld or closure to be checked. To provide for a defined 2.2-fold increase in volume and a 1.33-fold increase of pressure, which values a hose conventional in the field of blood transfusion must be able to resist according to ISO standard 3826, the expansion space has the same width as the first or the second clamping space. By varying the width of the expansion space, the device can be used for different kinds of hoses.

In order not to damage the first and second hose portions to be clamped, in the inserted position the clamping space has a defined dimension of twice the wall thickness of the hose to be clamped, which can be obtained, for instance, by a spacer arranged on one of the two clamping members.

To enable a fast and accurate determination of a leak in the connecting weld or closure to be checked, the device can comprise a detection system which in a first embodiment consists of an electric circuit with a microswitch arranged in the expansion space, which microswitch is operated by the expanded hose portion. In a second embodiment, the detection system consists of an electric circuit with a circuit breaker element, arranged in the expansion space, which becomes conductive upon contact with a fluid. Further, the device can comprise safety means in order to prevent fluid egress from the device.

The invention also relates to a device for checking for tightness a closure which is arranged at the end of a flexible fluid-filled hose, the device comprising two clamping members slidable relative to each other, each having a gripping face, and forming a clamping space in an inserted position, and further comprising a folding element, the arrangement being such that a hose portion can be folded and clamped in the clamping space, so that the fluid present in the hose portion is pressed to another hose portion including the closure to be checked, which other hose portion can expand on the outside of the device.

BRIEF DESCRIPTION OF THE DRAWINGS

Hereinafter the invention will be explained in detail on the basis of an exemplary embodiment, with reference to the drawings, wherein.

DETAILED DESCRIPTION OF THE INVENTION

Figure 1:
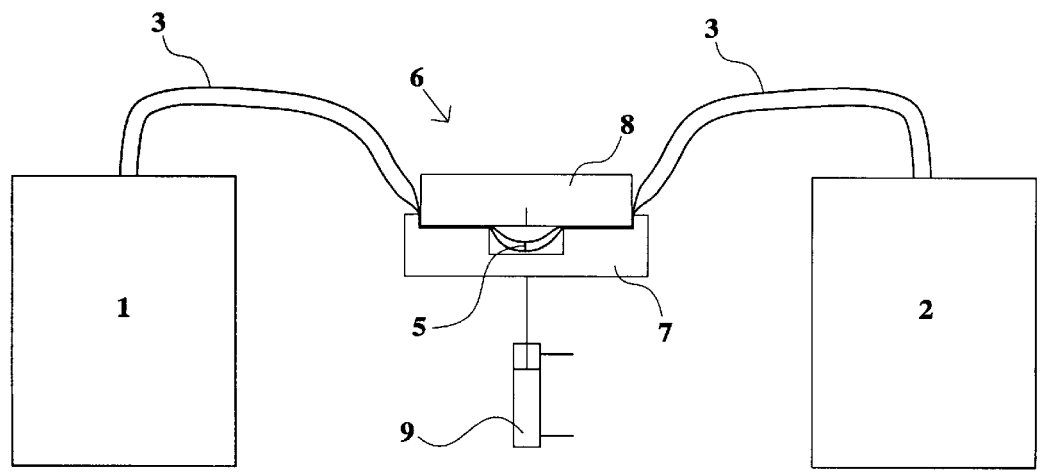
FIG. 1 is an elevation of two fluid bags connected with flexible hoses via a connecting weld, with the connecting weld placed in the device according to the invention for the purpose of checking it for tightness.

FIG. 1 shows two fluid bags 1, 2 with flexible hoses 3, 4, which are coupled to each other by means of a connecting weld 5. In order to be checked for tightness, the connecting weld 5 is placed in the device 6 according to the invention, which comprises a first clamping member 7 and a second clamping member 8, which are slidable relative to each other, for instance by means of a pneumatic cylinder 9 connected to the first clamping member 7.

Figure 2:
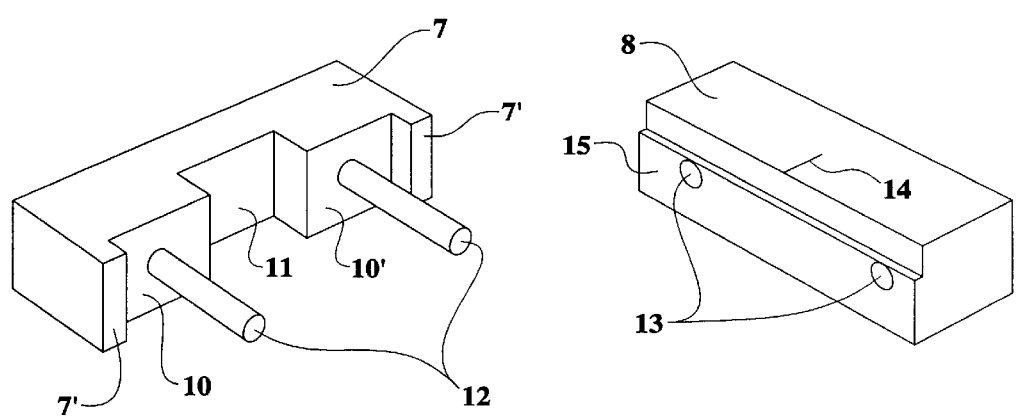
FIG. 2 is a perspective view of the two clamping members of the device according to the invention.

FIG. 2 is a perspective view of the two clamping members 7, 8 of the device 6 according to the invention. The first clamping member 7 is laterally provided with two folding elements 7', which embrace the second clamping member 8 in an inserted position. Further, the first clamping member 7 comprises an expansion space 11 located centrically between two gripping faces 10, 10'. The expansion space 11 has the same width as each of the two gripping faces 10, 10', which, with conventional hoses in the field of blood transfusion, leads to a 2.2-fold increase of volume and a 1.33-fold increase of pressure. Further, the first clamping member 7 possesses pins 12 which cooperate with guiding openings 13 in the second clamping member 8 for the directed displacement of the two clamping members 7, 8 towards and away from each other. At the top the second clamping member 8 is provided with an auxiliary line 14 for accurately placing the connecting weld 5 in the device 6. The front face of the second clamping member 8 is provided with a spacer 15, dimensioned so that the device 6 in the inserted position defines clamping spaces 16, 16' (see FIG. 4), which have a defined dimension of twice the wall thickness of the hose to be clamped.

Figure 3:
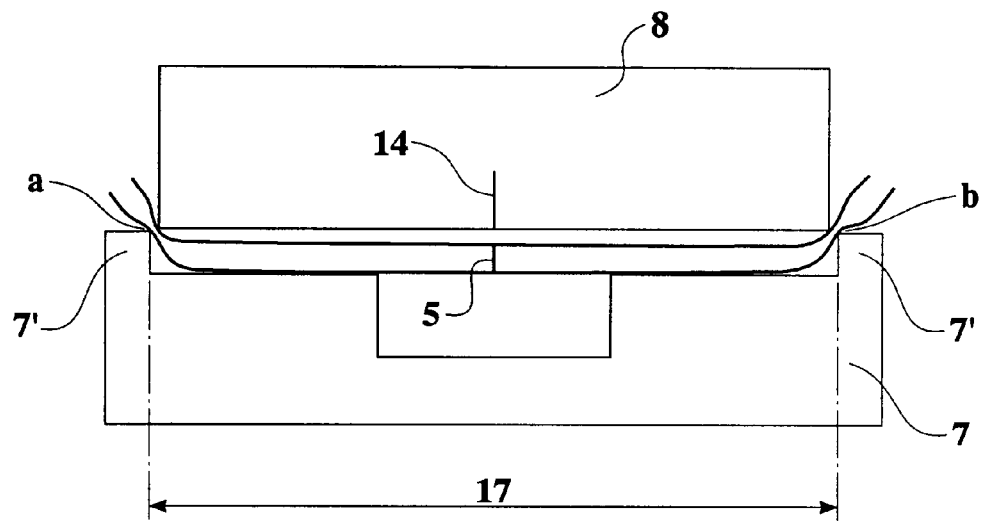
FIG. 3 is a ton plan view of the two clamping members during the insertion movement.

FIG. 3 is a top plan view of the two clamping members 7, 8 with the hose portion 17 placed between them, during the insertion movement. The connecting weld 5 is placed at the position of the auxiliary line 14 provided on the second clamping member 8. The folding elements 7' arranged on the side of the first clamping member 7 fold the hose at points a and b, such that the hose portion 17 with the fluid present therein is closed off from the remainder of the hose.

Figure 4:
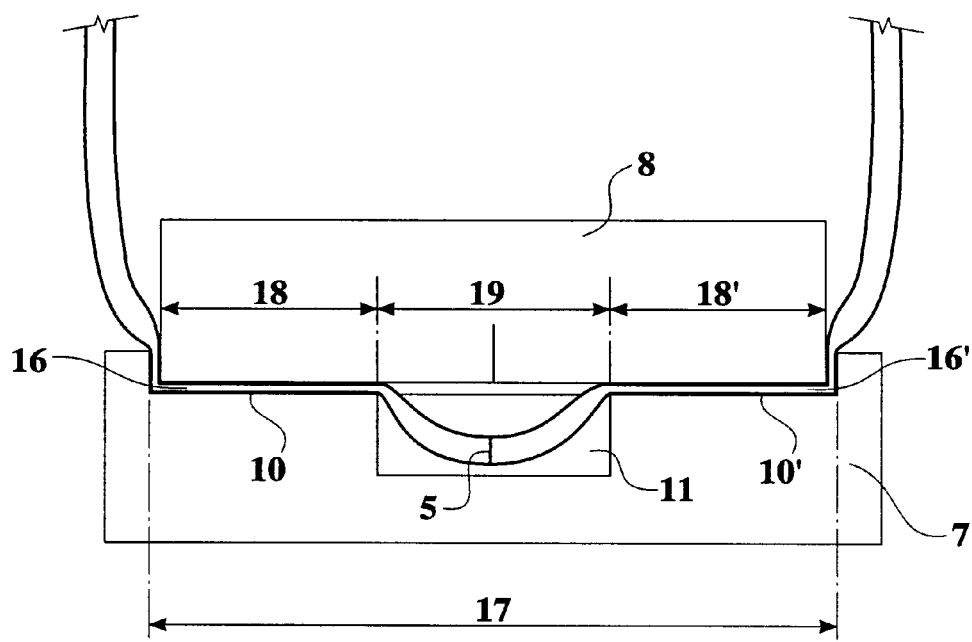
FIG. 4 is a ton plan view of the device according to the invention with the two clamping members in a position displaced towards each other.

FIG. 4 is a top plan view of the two clamping members 7, 8 in inserted position, with the hose portion 17 clamped between the two clamping members 7, 8, a first hose portion 18 being clamped between the clamping member 8 and a first gripping face 10 and a second hose portion 18' being clamped between the clamping member 8 and a second gripping face 10', in such a manner that the fluid present in the hose portion 17 is pressed to a third hose portion 19 including the connecting weld, which third hose portion 19 expands in the expansion space 11. In this way, a simple and inexpensive check of the connecting weld 5 or of a closure is possible.

Figure 5:
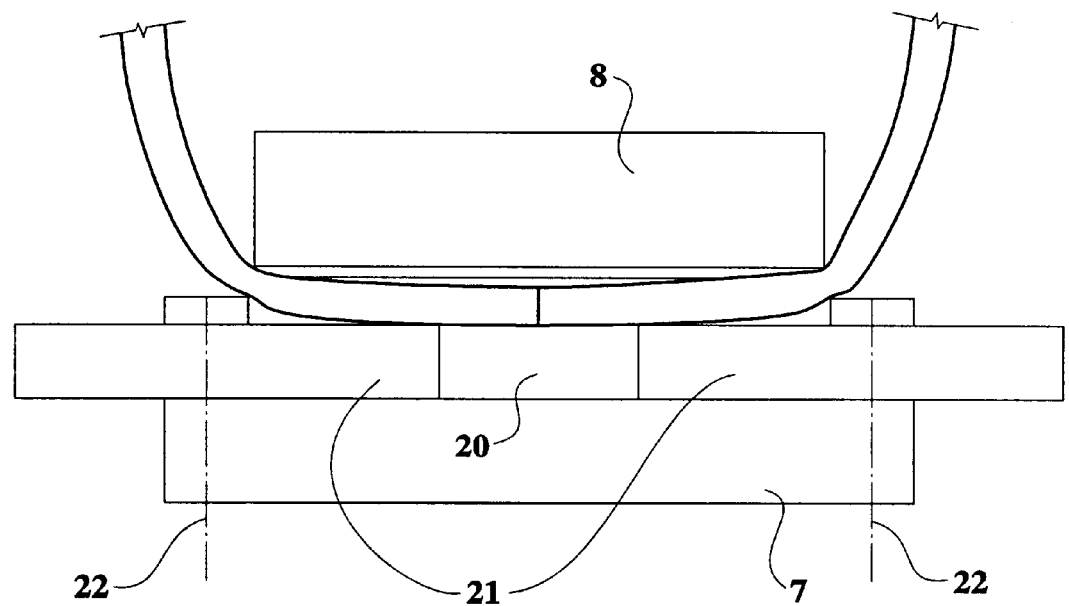
FIG. 5 shows a first clamping member with a variable expansion space.

FIG. 5 shows an alternative embodiment of the first clamping member 7, with a variable expansion space 20 which is defined by two adjusting elements 21 slidably bearing-mounted in the first clamping member. These adjusting elements 21 can be fixed by means of adjusting screws 22.

Figure 6:
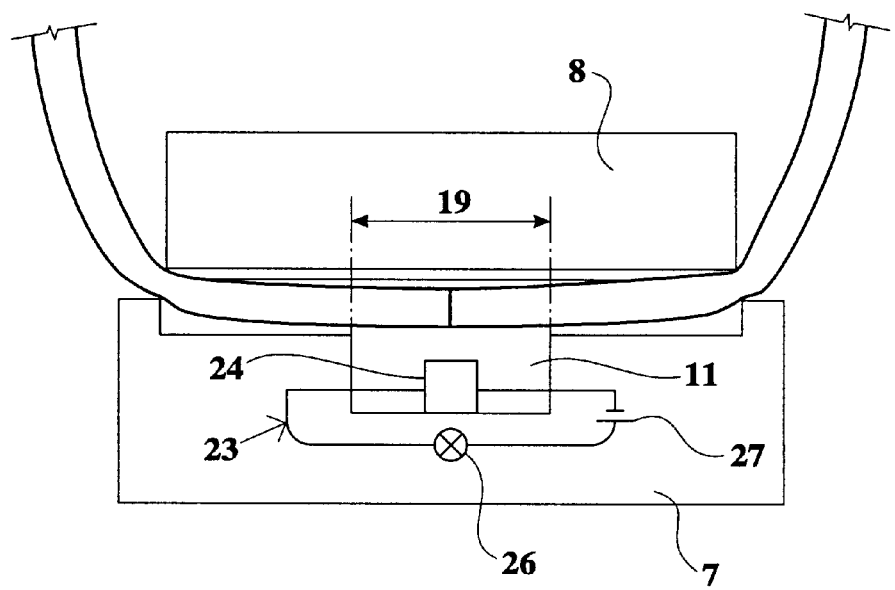
FIG. 6 shows a first clamping member with a first detection system.

FIG. 6 shows an embodiment of the first clamping member 7 wherein this clamping member 7 is provided with a first detection system 23, which comprises an electric circuit with a power source 27, a microswitch 24 arranged in the expansion space 11, a buzzer or a lamp 25. The microswitch can be operated by the expanded third hose portion 19, whereby the electric circuit is closed and a sound or light signal is generated. Any leak in the connecting weld 5 or closure to be checked makes it impossible for the third hose portion 19 to expand sufficiently in the expansion space 11 to operate the switch 24, so that this switch 24 is operated only when the connecting weld 5 is faultless.

Figure 7:
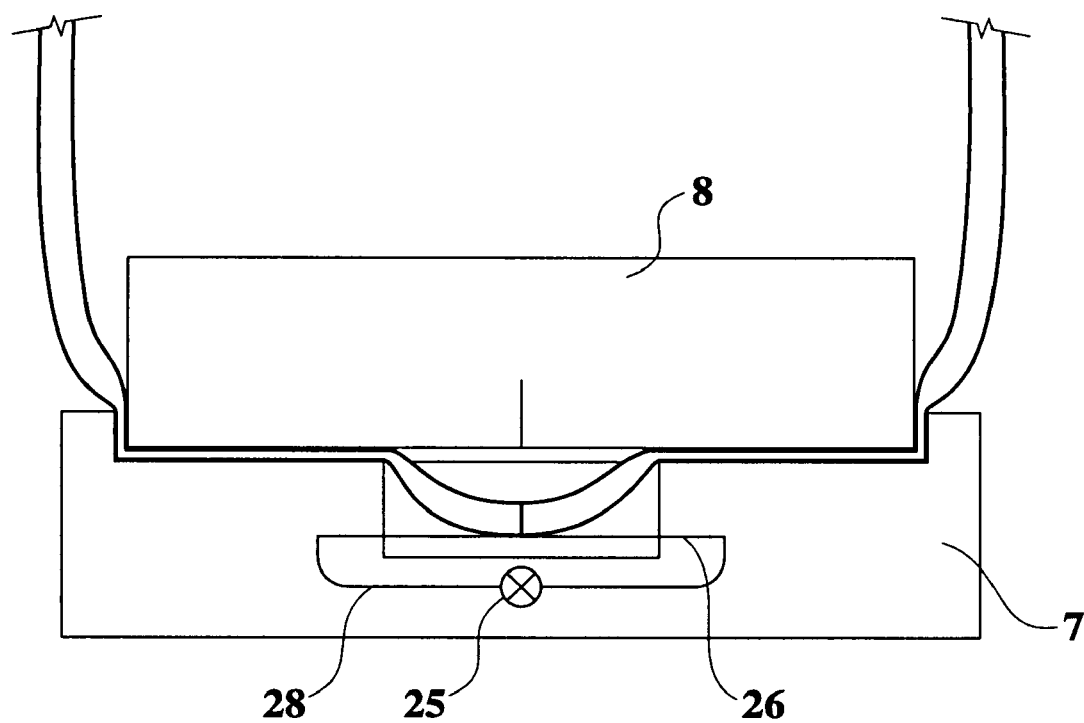
FIG. 7 shows a first clamping member with a second detection system.

FIG. 7 shows an embodiment of the first clamping member 7 wherein this clamping member 7 is provided with a second detection system 28, which comprises an electric circuit which is interrupted by means of a circuit breaker element, for instance a membrane 26 of paper. In case of leakage, the circuit breaker element 26 becomes conductive as a result of the egressive fluid and the electric circuit is closed, which is again signalled by means of a light or sound signal.

It goes without saying that many other modifications and variants are possible within the scope of the invention. For instance, the defined clamping space may also be provided, for example, by the driving mechanism, with the clamping member to be moved being displaced only as far as a particular position. Also, the folding elements may be arranged separately from the two clamping members. Further, it is possible for the device to be used only for checking a closure, the device consisting of a folding element and two clamping members slidable relative to each other, each clamping member having a gripping face, the arrangement being such that the hose portion with the closure to be checked can expand on the outside of the device.

What is claimed is:

1. A device for checking the tightness of a closure or a connecting weld provided in a flexible fluid-filled hose, comprising;

a first clamping member and a second clamping member slidable relative to each other, said members when placed in an operative position forming (i) a first clamping space; (ii) a second clamping space and; (iii) an expansion space between said first and second clamping spaces;

one of said clamping members including folding elements which embrace the opposing clamping member when the clamping members are in an operative position, wherein a fluid-filled hose having a first hose portion and a second hose portion which when positioned in the first and second clamping spaces causes fluid present in the first and second hose portions to be pressed to a third hose portion which is disposed in said expansion space and which includes the closure or connecting weld to be checked.

2. The device of claim 1, further including means for moving the clamping members toward and away from each other, said moving means selected from the group consisting of mechanical, electrical, hydraulic and pneumatic means.

3. The device of claim 1, wherein the first and second clamping spaces are defined by a first gripping face and a second gripping face on the first clamping member and by a corresponding gripping face on the second clamping member, and wherein the expansion space between the two gripping faces of the first clamping member is formed by a recess in the surface thereof, which cooperates with the gripping face of the second clamping member (8).

4. The device of claim 1, wherein the device further comprises means for directed displacement of the two clamping members away from and towards each other.

5. The device of claim 4, wherein said means for the directed displacement of the two clamping members consist of two pins projecting from the gripping faces on the first clamping member and two openings formed in the gripping face of the second clamping member.

6. The device of claim 1, wherein said folding elements are arranged on the sides of one of said clamping members so as to embrace the other clamping member when said clamping members are in an operative position, said folding elements effective to fold the ends of the first and the second hose portions.

7. The device of claim 1, characterized in that the first and second clamping spaces have the same width.

8. The device of claim 7, characterized in that the expansion space has the same width as the first or the second clamping space.

9. The device of claim 1, characterized in that the width of the expansion space is variable.

10. The device of claim 1, characterized in that at least one of said first and second clamping spaces has a defined dimension of twice the wall thickness of the hose to be clamped.

11. The device of claim 10, characterized in that one of said first or second clamping members is provided with a spacer which defines the dimension of the at least one clamping space.

12. The device of claim 1, characterized in that at least one of said first or second clamping members comprises on its top surface an auxiliary line for placement of the connecting weld or closure to be checked.

13. The device of claim 1, characterized in that the device further comprises a detection system.

14. The device of claim 13, characterized in that the detection system comprises a microswitch which is arranged in the expansion space and which is operated by the expanded hose portion.

15. The device of claim 13, characterized in that the detection system comprises a circuit interrupter element which is arranged in the expansion space and which becomes conductive upon contact with fluid.

* * * * *